United States Patent [19]

Kimmel et al.

[11] Patent Number: 5,670,321

[45] Date of Patent: Sep. 23, 1997

[54] EFFICIENT METHOD TO CONDUCT LARGE-SCALE GENOME SEQUENCING

[75] Inventors: Bruce E. Kimmel, San Mateo; Michael Ellis; David Ruddy, both of San Francisco, all of Calif.

[73] Assignee: Mercator Genetics, Inc., Menlo Park, Calif.

[21] Appl. No.: 438,567

[22] Filed: May 10, 1995

[51] Int. Cl.⁶ .............................. C12Q 1/60; C12Q 1/78; C12P 19/34; C07H 21/04

[52] U.S. Cl. .................. 435/6; 435/5; 435/91.2; 536/24.3; 536/24.33; 536/24.32

[58] Field of Search .................... 435/6, 5, 91.2; 536/24.3–24.33

[56] References Cited

PUBLICATIONS

Roach et al. Genomics 26: 345–353 1995.
Stratham et al. PNAS 88: 1247–1250 1991.
Michael Strathmann, et al., Proc. Natl. Acad. Sci. USA vol. 88, pp. 1247–1250, Feb. 1991, Transposon–facilitated DNA sequencing.
Ellson Y. Chen, et al., Genomics 17, 651–666 (1983) Ordered Shotgun Sequencing, a Strategy for Integrated Mapping and Sequencing of YAC Clones.

*Primary Examiner*—W. Gary Jones
*Assistant Examiner*—Dianne Rees
*Attorney, Agent, or Firm*—Townsend & Townsend & Crew LLP

[57] ABSTRACT

An efficient method for sequencing large fragments of DNA is described. A subclone path through the fragment is first identified; the collection of subclones that define this path is then sequenced using transposon-mediated direct sequencing techniques to an extent sufficient to provide the complete sequence of the fragment.

4 Claims, No Drawings

1

EFFICIENT METHOD TO CONDUCT LARGE-SCALE GENOME SEQUENCING

FIELD OF THE INVENTION

The invention is in the field of determining the nucleotide sequence of large segments of DNA. More specifically, the invention provides an improved method to obtain the complete nucleotide sequence of genomic DNA provided in fragments of over 30 kb.

BACKGROUND ART

Methods currently used to sequence large segments of DNA do not lend themselves to large-scale determination of genomic sequences. In general, the initial determination of a genomic clone sequence results in ambiguities and discrepancies that are resolved by assembling and editing the raw sequencing data into a consensus sequence. There are also, generally, holes in the sequence that need to be filled in in order to create a finished sequence. There are two general strategies for obtaining the initial sequence: shotgun sequencing and transposon-mediated directed sequencing.

Shotgun sequencing is reasonably appropriate for generating the initial sequences of the genomic clone. In this method, the clone is digested with a multiplicity of restriction enzymes and the individual fragments are sequenced. When sufficient sequence is obtained to putatively cover the length of the genomic clone (1×total sequence length) statistically 65% of the genomic clone sequence will have successfully been determined. The shotgun strategy relies on assembly algorithms to piece together a final sequence by determining relationships between a selected set of random templates. Although this assembly process is semiautomated, it remains labor-intensive, especially in complex regions that contain highly related tandem repeats. In addition, since the selection of subclones is not random, gaps of unknown distance are included between islands of known sequence. Linking up the islands requires either sequencing additional subclones or ordering custom oligonucleotides to generate sequence into the gaps. The weaknesses of shotgun sequencing performed on substantial lengths of nucleotide sequence are thus 1) the difficulties involved in sequence assembly and 2) the need for hole-filling.

On the other hand, the transposon-mediated sequencing method described by Strathmann, M. et al. *Proc Natl Acad Sci USA* (1991) 88:1247–1250, provides an orderly approach to generating subclones for sequencing. The method uses a γδ bacterial transposable element bracketed by sequencing primers. The primer-flanked γδ transposon permits the introduction of evenly spaced priming sites across a fragment with an unknown DNA sequence. The number of template sequences required to obtain the complete sequence information can be calculated from the length of the fragment. As the transposon insertions are random, the positions of the insertions are mapped, for example, using the polymerase chain reaction (PCR) using primers that amplify the intervening sequence between the transposon insertion site and the vector sequences at each end of the inserted fragment to be sequenced. The lengths of the amplified products thus define a map position for the transposon. Sequencing can be conducted based on the sequencing primers flanking the transposon, and since the position of the transposon has been mapped prior to sequencing, a fully automated assembly process is possible. There are no gaps since an ordered set of sequencing templates which cover the DNA fragment is produced.

However, transposon sequencing can only be used on fragments containing 2–5 kb; preferably 3–4 kb. Thus, to use the transposon method on larger fragments, smaller subclones of the original fragment must be generated and organized into an ordered overlapping set. The shotgun strategy is not completely appropriate for this purpose. Neither is an alternative strategy termed dog-tagging. Dog-tagging is a "walking" process that scans through a 30-hit subclone library for sequences that are near the end of the last walking step. It is labor-intensive and does not always succeed.

The present invention provides a large-scale sequencing method which combines efficient method to generate a subclone path through the large original fragment, such as a genomic clone, wherein the subclones are accessible to transposon sequencing, in combination with sequencing these subclones using the transposon method.

DISCLOSURE OF THE INVENTION

The invention provides a systematic and efficient way to sequence large fragments of DNA, in particular genomic DNA. It combines an end-sequencing-based method of subclone pathway generation through the fragment with efficient transposon-based sequencing of the identified subclones.

Thus, in one aspect, the invention is directed to a method to sequence a fragment of DNA, said fragment typically having a length of more than about 30 kb. The method comprises the following steps.

First, the fragment is provided in a host cloning vector capable of accommodating it. The size of the fragment that can be sequenced will depend on the nature of the host cloning vector. Cloning vectors are available that can accommodate large fragments of DNA; even the approximately 30–40 kb fragments that are suitable for insertion into cosmids are of sufficient length that the method of the invention is usefully applicable to them.

A composition comprising said vector containing the inserted fragment is then randomly sheared, such as by sonication, to obtain subfragments of approximately 3 kb. The length of the subfragments is appropriate to the transposon-mediated directed sequencing method that will ultimately be applied. The 3 kb length is an approximation; it is intended only as an order of magnitude. Generally speaking, subfragments of 2–5 kb are susceptible to this approach.

The subfragments are then inserted into host cloning vectors to obtain a library of subclones. These host cloning vectors are ideally of minimal size, containing only a selectable marker, an origin of replication, and appropriate insertion sites for the subfragments. The desirability of minimizing the available plasmid DNA in the performance of transposon-mediated sequencing is described by Strathmann, et al. (supra).

Sufficient subclones that contain subfragments derived from the original fragment are then recovered to provide 1× coverage of the fragment when the end of each subfragment is sequenced. A stretch of about 400–450 bases can be sequenced with assurance using available automated sequencing techniques. Thus, the sequencing can be conducted using the sequencing primers based on the vector sequences adjacent the inserts to proceed into the insert to approximately this distance. For a 1× coverage of the original fragment, the number of subclones required can be calculated by dividing the length of the original fragment by the intended sequencing distance—i.e., by approximately 400–450.

There should also be sufficient subclones in the library so that when the complete sequence of each is determined, the coverage of the original fragment will be about 7–8×. This provides, as described below, a high probability that every nucleotide present in the fragment will be present in the library. This number can, of course, be determined by multiplying the length of the fragment by 7 or 8 and dividing by the length of the subfragments generated.

It is preferable to assure that all of the subclones in the library contain pieces of the original fragment. This can be done by recovering only those subclones that hybridize to the fragments.

A sufficient portion of one of the ends of each recovered subclone containing fragment-derived DNA is then sequenced and this sequence information is placed into a searchable database. The database is searched for subclones that contain subfragments with nucleotide sequences matching those that characterize the host vector that accommodated the original fragment. To the extent that these subfragments also contain sequence from the original fragment, that sequence must be at one or the other end of the original fragment. This illustrates why the efficiency of the method is improved by introducing a prescreening step which eliminates any subclones which do not contain portions of the original fragment. If the prescreening has been done, these subclones contain oligonucleotide sequence from either end of the original fragment. The identified subclones are recovered.

A partial sequence of each of the identified subclones is determined from the opposite end of the subfragment insert from that originally placed in the database. This provides "second end" sequence information concerning sequence further removed from the end of the original fragment. This information is then used to search the database in order to identify subclones containing nucleotide sequence that matches this second end sequence. Such subclones are likely to represent regions of the original fragment that are farther removed from the ends and provide further progress in constructing a path across the fragment. These subclones are recovered as well, and sequenced from the end opposite to that which was sequenced to provide the information for the database and this new information, in turn, used to search the database for a matching sequence. The steps of second end sequencing, searching the database with the resulting sequence information, and recovery of subclones which contain a match are repeated sequentially until subclones have been identified that represent the complete original fragment. The resulting collection of subclones consists of an ordered minimum set that collectively represent the original fragment. The appropriate sequence of such subclones to span the original fragment from end to end is also known.

It remains only to obtain sufficient portions of the complete nucleotide sequence of each subclone from the subclone collection using transposon-mediated sequencing to provide the complete sequence of the original fragment.

In another aspect, the invention is directed to kits suitable for conducting the method of the invention.

MODES OF CARRYING OUT THE INVENTION

The process begins with a fragment of DNA, such as a genomic fragment, which is inserted into an appropriate host vector capable of accommodating it. For example, a BAC vector can accommodate approximately 140 kb of DNA; a cosmid vector can accommodate approximately 40 kb. A composition comprised of these insert-containing vectors is randomly sheared using standard methods, such as sonication, to obtain fragments suitable for transposon-based sequencing—i.e., about 2–5 kb, preferably 3–4 kb, on the average.

The resulting subfragments are ligated into cloning vectors to create a first library of subclones representing the original fragment. Because the subclones in this library will be used as target plasmids for transposon-mediated sequencing, the size of the cloning vector should be minimized; preferably it should contain only a selectable marker, an origin of replication, and an insertion site. A suitable host plasmid is pOT2; the subfragments obtained by shearing the original composition are end-repaired, ligated to suitable restriction site containing adapters, and inserted into the host vector. Suitable adapters for the pOT2 vector contain BstXI sites.

The resulting cloning vectors with their inserts are then transfected into bacteria, typically $E.$ $coli$, for clonal growth. This first library should contain a 15–20-fold representation of the original fragment of DNA. For example, if the original fragment is approximately 40 kb, and the subclones contain inserts of approximately 4 kb, 200 such clones would be required for a 20-fold representation of the original fragment.

As pointed out above, this first library will contain subclones which do not contain DNA derived from the original fragment to be sequenced. In order to eliminate these subclones, a preliminary hybridization screen is conducted. The required number of subclones is prepared for hybridization screening, for example, by plating in 96-well plates and transferring to filters. The filters are then probed with the original fragment insert to weed out any colonies which do not contain DNA which represents portions of the original fragment. This checks the quality of the library and eliminates subclones that contain only host cloning vector for the original fragment or contaminating bacterial DNA.

The subclones confirmed to contain inserts derived from the fragment to be sequenced form a second library. The number of subclones in this library should be sufficient to contain a 7–8× representation of the fragment. Each subclone is individually sequenced from one end of the insert. This is straightforward, since the sequence information in the cloning vector provides sufficient information to design appropriate primers. Typically, about 400–450 nucleotides into the insert is read. In addition to the requirement for 7–8× coverage of the fragment when the complete insert sequences of the subclones are obtained, there must be sufficient sequence information available from this end sequencing to represent a 1× coverage of the fragment. Thus, if the original fragment contained 40 kb and 400 nucleotides into the insert is read, 100 clones would be required. The resulting sequence information is organized into a computer-readable form for searching. A DNA sequence comparison algorithm can be used for subsequent comparisons, such as the NCBI program BLASTN.

The criteria used to determine the number of subclones used to establish the database in the method described above are that low sequencing redundancy must be maintained and a complete path must be available within the set of subclones chosen to provide complete coverage of the original fragment. In addition, the number must be chosen so that there is a high probability of finding the next subclone when searching with the newly sequenced end sequence.

A method similar to that employed by Chen, E. et al. $Genomics$ (1993) 17:651–666, is used. Lander and Waterman (cite) conclude that the maximum number of sequence islands occurs at $C=(1-\theta)^{-1}$, where C is the sequence coverage and $\theta$ is the ratio of the number of bases required to detect the true overlap to the sequence read length. As $\theta$ approaches zero, sequence coverage of 1 will produce the maximum number of sequence islands. In order to achieve the highest efficiency database, enough end-sequence data should be generated to obtain about 1× coverage.

In addition, the subclone coverage—i.e., the redundancy based on the complete sequence contained in the number of subclones chosen—is important. A subclone coverage factor of 7×–8× provides a 99.9% probability that each nucleotide in the fragment will actually reside in the library. This requires only about 100 subclones averaging 3 kb in size for a 40 kb fragment.

Sequence information from the host vector for the original fragment is used as the first query and reveals which subclones in the library are hybrid vector/fragment insert subclones. These will identify the two ends of the original fragment. One subclone representing each end, preferably that containing the least amount of vector sequence, is selected for further sequencing. The insert of the identified subclone will be sequenced from the opposite end from that previously sequenced—i.e., opposite the end containing the vector sequence. The new sequence information (which is now derived from the fragment) is used as the next query. This identifies additional subclones which contain additional nucleotide sequence farther in from the end of the original fragment. The next identified subclone is then also sequenced from the opposite end of the insert from that used to place it in the database and the new sequence information used as the next query. The process is continued sequentially until a subclone path through the fragment is obtained. The subclone path will represent the collection of subclones which completely define the fragment from which they originated, and their correct relative positions are known.

At any point in this process, if there are no responses to the query, additional sequence can be obtained from the subclones already identified and this sequence used as the query.

Once the subclone path is determined, it remains only to complete the sequencing of the subclones involved in the path. According to the method of the invention, this is accomplished using the transposon-mediated method of Strathmann incorporated by reference hereinabove. Use of this method to complete the sequence information for the fragment has been designated "minimal assembled path" (MAP) sequencing. The name is apt because the information provided by the subclone path can be used to determine the minimal sequencing path through the identified subclones. For example, if two subclones overlap over 1 kb, transposon insertions can be selected so that the overlap region is sequenced only once. Thus, although theoretically each of the subclones obtained to define the path can be completely sequenced using the transposon-mediated method, only sufficient portions of these subclones need be sequenced to obtain the complete sequence of the original fragment.

We claim:

1. A method to determine the nucleotide sequence of a fragment of DNA, said fragment having a length of more than about 30 kb, which method comprises:

(a) providing said fragment in a first host cloning vector;

(b) shearing a composition comprising said vector containing the inserted fragment under conditions to obtain subfragments of approximately 2–5 kb;

(c) inserting each of said subfragments into a second host cloning vector to obtain a first library of subclones;

(d) recovering sufficient subclones from said first library of subclones to provide 1× coverage of the fragment when about 400 bases at one end of each of said subfragments is sequenced and about 7–8× coverage of the fragment when the complete nucleotide sequence of each of the subfragments are determined;

(e) sequencing about 400 bases at a first end of each of said subfragments in the recovered subclones to obtain first end sequence information;

(f) placing the first end sequence information into a searchable database;

(g) searching said database to identify subclones containing subfragments that include nucleotide sequences that match vector sequences present in the first host cloning vector;

(h) recovering the identified subclones;

(i) sequencing about 400 based at a second end of the subfragment of each of the identified subclones, said second end opposite from the first end sequenced in step (e), to obtain second end sequence;

(j) searching the database to identify subclones containing subfragments that include nucleotide sequences that match said second end sequence;

(k) recovering the identified subclones;

(l) sequentially repeating steps (i)–(k) until a collection of subclones has been identified that represents the complete fragment; and (m) obtaining a sufficient portion of the complete nucleotide sequence of the subfragment contained in each of the subclones from the collection, using transposon-mediated sequencing, to obtain the complete sequence of the fragment.

2. The method of claim 1 which further comprises screening the first library created in step (c) to include only subclones containing DNA sequences from the fragment to provide the subclones recovered in step (d).

3. The method of claim 1 wherein the first host cloning vector is a cosmid.

4. The method of claim 1 wherein said transposon-mediated sequencing employs the γδ transposon flanked by priming sequences.

* * * * *